(12) United States Patent
Vesey

(10) Patent No.: US 7,186,502 B2
(45) Date of Patent: Mar. 6, 2007

(54) PROCESS FOR PREPARING CONTROL SAMPLES OF PARTICLES SUCH AS MICROORGANISMS AND CELLS

(75) Inventor: Graham Vesey, New South Wales (AU)

(73) Assignee: BTF Pty, Ltd., Fairlight (AU)

( * ) Notice: Subject to any disclaimer, the term of this patent is extended or adjusted under 35 U.S.C. 154(b) by 0 days.

(21) Appl. No.: 10/221,620

(22) PCT Filed: Mar. 12, 2001

(86) PCT No.: PCT/AU01/00267

§ 371 (c)(1),
(2), (4) Date: Nov. 8, 2002

(87) PCT Pub. No.: WO01/68902

PCT Pub. Date: Sep. 20, 2001

(65) Prior Publication Data

US 2003/0186331 A1    Oct. 2, 2003

(30) Foreign Application Priority Data

Mar. 16, 2000    (AU) .................................. PQ6291

(51) Int. Cl.
*C12Q 1/00*    (2006.01)
(52) U.S. Cl. .................. 435/4; 435/5; 435/7.1; 435/7.2; 435/7.91; 436/50; 436/55; 436/174; 422/119; 422/67
(58) Field of Classification Search .............. 435/4, 435/5, 7.1, 7.2, 91, 7.91; 436/50, 55, 174; 422/119, 67
See application file for complete search history.

(56) References Cited

U.S. PATENT DOCUMENTS

| 5,578,460 | A |   | 11/1996 | Ebersole et al. ............... 435/29 |
| 6,071,689 | A | * | 6/2000 | Seidel et al. ..................... 435/2 |
| 6,129,893 | A | * | 10/2000 | Bolton et al. .................. 422/23 |
| 6,225,046 | B1 | * | 5/2001 | Vesey et al. .................... 435/5 |
| 6,281,018 | B1 | * | 8/2001 | Kirouac et al. ............... 436/63 |
| 2002/0102245 | A1 | * | 8/2002 | Hermeking et al. ....... 424/94.1 |

FOREIGN PATENT DOCUMENTS

| GB | 2 316 081 A | 2/1998 |
| WO | WO 97/08204 A1 | 3/1997 |
| WO | WO 00/12191 A1 | 3/2000 |
| WO | WO 01/09281 A1 | 2/2001 |

OTHER PUBLICATIONS

Reynolds et al. J. Appl. Microbiology 1999 vol. 87, p. 804-813.*
Reynolds DT et al., "Detection of Cryptosporidium oocysts in water: techniques for generating precise recovery data," Journal of Applied Microbiology, 1999, 87:804-813.
C. A. Morgan et al., "Production of Precise Microbiology Standards Using Flow Cytometry and Freeze Drying", *Cytometry; J. Society Analytical Cytology*, vol. 62 A, No. 2 (Dec. 2004), pp. 162-168.
M. Warnecke et al., "Evaluation of an internal positive control for *Cryptosporidium* and *Giardia* testing in water samples", *Letters in Applied Microbiology*, vol. 37, No. 3 (2003), pp. 244-248.
D. T. Reynolds & C. R. Fricker "Application of laser scanning for the rapid and automated detection of bacteria in water samples", *Journal of Applied Microbiology*, vol. 86, No. 5 (May 1999), pp. 785-795.
Jason W. Bennett et al., "A Comparison of Enumeration Techniques for *Cryptosporidium parvum* Oocysts", *J. Parasitol.*, Am. Soc. Parsitologists, vol. 85, No. 6 (Dec. 1999), pp. 1165-1168.
G. Vesey et al., "Simple and Rapid Measurement of *Cryptosporidium* Excystation Using Flow Cytometry", *International J. Parasitology*, Au. Soc. Parasitology, Published by Elsevier Science Ltd., Printed in Great Britain, vol. 27, No. 11 (Nov. 1997), pp. 1353-1359.
Graham Vesey et al., "Application of Flow Cytometric Methods for the Routine Detection of *Cryptosporidium* and *Giardia* in Water", *Cytometry*, Wiley-Liss, Inc., vol. 16, No. 1 (May 1994), pp. 1-6.

* cited by examiner

*Primary Examiner*—Long V. Le
*Assistant Examiner*—Jacob Cheu
(74) *Attorney, Agent, or Firm*—Cooley Godward Kronish LLP

(57) ABSTRACT

Processes for preparing controlled samples of particles, including microorganisms and cells are described. A sample of particles is provided and separated into a predetermined number of desired particles by particle separation means. The predetermined number of particles is dispensed into a receptacle or onto a surface in accordance with a sorting instruction, with the receptacle or surface being positioned by collecting means so as to receive the dispensed particles. A sorting instruction from the particle dispensing means activates the collecting means such that when a sorting instruction has been actuated, so as to deliver a predetermined number of particles into a receptacle or onto a surface which is positioned accurately for sufficient time to collect all sorted particles, the collecting means advances and positions a subsequent surface or receptacle for receipt of particles, the collector means thereafter signaling the particle separation means to commence the next sorting instruction.

16 Claims, No Drawings

US 7,186,502 B2

PROCESS FOR PREPARING CONTROL SAMPLES OF PARTICLES SUCH AS MICROORGANISMS AND CELLS

This is a National stage entry under 35 U.S.C. § 371 of application No. PCT/AU01/00267 filed Mar. 12, 2001; the disclosure of which is incorporated herein by reference.

This invention relates to a process for the preparation of samples containing predetermined numbers of small particles such as cells, bacteria, protozoa, yeast, fungi, spores, pollen and viruses.

Note: References are collected at the end of the specification.

BACKGROUND OF THE INVENTION

There are many instances where cells or microorganisms are measured in liquids or solids. Samples such as air, water, food, beverages and clinica samples are: routinely tested with various microbiological methods. It is essential that these tests are performed accurately, reliably and that results are comparable between samples and between laboratories.

The testing methods used vary greatly but all involve some manipulation of the sample. Examples include flotation, pipetting, centrifuging filtering, or homogenising. Losses of the sample and losses of cells or microorganisms will occur during these manipulations. These losses will vary between different types of samples. Some methods may also involve various pre-treatments such as heating, freezing, shaking, mixing or pH adjustment. These treatments may also cause losses of the cells or microorganisms. All testing methods involve a detection process and may also involve enumeration of the particles recovered. This may be a simple process such as counting colonies on an agar plate or it may be a complex analytical process such as flow cytometry or immunomagnetic separation. All these detection and enumeration processes will have inaccuracies that will effect the result of the test.

Quality control (QC) is routinely performed to check the accuracy of a test method and to determine what losses of cells or microorganisms are occurring during the testing process. The QC process often involves the analysis of a sample that has been seeded with specific cells or microorganisms. The number of cells or microorganisms that were seeded into the sample are then compared to the number detected.

The QC process relies on the availability of control samples that contain known numbers of cells or microorganisms. These control samples must be reliable and the numbers within each sample must be accurate. Such control samples are difficult to prepare, are often not stable and are not widely available.

Water is routinely tested for the presence of *Cryptosporidium* and *Giardia*. The testing method involves numerous processes in which organisms can be lost (Vesey et al., 1994a). It is, therefore, important to perform stringent quality control the performance of the methodology. Quality control can involve analysing a standard that contains a known number of cysts and oocysts. Preparation of standards using conventional techniques such as pipetting result in inaccurate preparations (Reynolds et al, 1999). Furthermore, preparations are not stable. Deterioration and clumping of the microorganisms occurs over time.

Flow cytometry has been shown to be useful for the preparation of accurate control material (Reynolds et a., 1999), however the method is tedious and time consuming and therefore, not suitable for large-scale production.

Cooling water and water distribution systems are routinely tested for the presence of *Legionella*. The testing method involves concentrating the bacteria in the water sample by centrifugation or filtration and then detecting the *Legionella* bacteria by either a culturing process, immunological techniques or molecular methods. Use of the culturing process is limited because it takes between 5 and 10 days to obtain a result.

It is essential that the immunological and molecular methods are stringently quality controlled because both methods are susceptible to false negative results. Quality control can involve analysing a standard that contains a known number of *Legionella* cells. However, accurate standards are difficult to prepare and are not stable. Preparations can be prepared using flow cytometry to analyse the light scatter of the cells and to sort the cells. If live *Legionella* cells are to be sorted then a aliquoting method that does not create aerosols, such as piezo cappillary dispensing, would be required to overcome biohazard risks.

A need accordingly exists for an automated, accurate, convenient and cost-effective process for producing control samples containing known numbers of cells or microorganisms.

The invention allows the automated preparation of control samples containing predetermined numbers of small particles such as microorganisms or cells. These samples containing the known number of microorganisms or cells may be gamma-irradiated or otherwise treated to prolong the stability and shelf life of the samples. A percentage of the samples may, be tested to confirm the number of microorganisms or cells in each sample.

SUMMARY OF THE INVENTION

In a first aspect, the present invention is concerned with a process for the automated preparation of control samples containing predetermined numbers of desired particles, particularly microorganisms or cells, said process comprising providing a sample of particles and separating a predetermined number of desired particles by particle separation means, dispensing the predetermined number of particles into a receptacle or onto a surface in accordance with a sorting instruction the receptacle or surface being positioned by collecting means so as to receive the dispensed particles, characterised in that a sorting instruction from the particle dispensing means activates the collecting means such that when a sorting instruction has been actuated so as to deliver a predetermined number of particles into a receptacle or onto a surface which is positioned accurately for sufficient time to collect all sorted particles, the collecting means advances and positions a subsequent surface or receptacle for receipt of particles, said collector means thereafter signalling the particle separation means to commence the next sorting instruction.

The particles are small particles, particularly those used for quality control and include cells (such as animal or plant cells), bacteria, protozoa, yeast, fungi, spores, pollen and viruses.

The particle separating means are preferably automated liquid handling separating means, such as a flow cytometer, a coulter particle separating apparatus, or-any other means which separates particles based on chemical, physical, biological, fluorescent or other properties.

A particular example of a particle separating means which may be used to dipsense and analyse particles is flow cytometry. Flow cytometry can be used to define the light scatter properties of microorganisms or cells (Shapiro, 1996;

Vesey et al., 1994b) or other particles. Flow cytometry allows preparation of a predetermined population of microorganisms or cells or other particles. A flow cytometer can be set to sort a defined number of particles such as microorganisms or cells, using the light scatter properties to distinguish the microorganisms from contaminating particles. The sorted microorganisms may then be collected in a receptacle, such as a test tube or tray or onto a surface such as a slide by collecting means such as a fraction collection. Once collection is complete a fresh receptacle is automatically moved into position and the flow cytometer is electronically signalled to begin sorting again.

Alternative particles separation means of dispensing or sorting particles includes Coulter sensing, or means which separate particles by measurement of impedance, magnetism, mass or specific gravity. Also, optical detection particles separation means using raman microscopy, light scatter, imaging, fluorescence, absorption and luminescence may be used.

Still further examples of particle separating means include piezo capillary dispensing, piezo actuated catcher tube, charged droplet deflection, acoustic manipulation (Standing Wave, Shock Wave), electrostatic manipulation, and optical tweezers.

The collector means may be a fraction collector, or any other device which allows multiple samples of a desired material to be collected.

The particle separating means and collecting means communicate electronically so that a sorting signal from the separating means actuates movement of a receptacle, surface or other means for receiving particles into a portion to receive separated particles. For example, an electrical output of a flow cytometer may be connected to the input of a fraction collector.

A receptacle may be any container, such as a test tube, vial, dish, membrane, slide or a well in multi-well plate or dish, which can preferably be closed after receipt of a sample of particles is delivered to it. Reference to a surface includes a slide or any other surface.

After preparation, the control sample may be irradiated, such as with gamma irradiation or UV irradiation, or otherwise inactivated/preserved or sterilised in a manner which does not effect the structural integrity of the particles or effect analysis or detection.

In another aspect, the present invention is concerned with a process for the automated preparation of controlled samples containing known numbers of microorganisms or cells, said process comprising:

(a) Analysing a sample of microorganisms or cells. The sample may be stained with a fluorescent antibody (or anything else that helps differentiate the target microorganisms from contaminating particles contained in the sample).

(b) Dispensing known numbers of microorganisms or cells into a receptacle or onto a surface that is positioned accurately for sufficient time to collect all sorted particles.

(c) Automatically moving the receptacle or surface out of the collection area and positioning another in the collection area.

(d) Automatically signalling the dispenser to dispense the particles.

(e) Automatically repeating the cycle until the required number of control samples have been prepared.

(f) Gamma irradiating the control samples.

(g) Performing analysis on a percentage of the control samples to confirm the number of microorganisms within the control samples.

(h) As a further quality control procedure every control sample is weighed.

(i) The control samples are used to determine the efficiency of a testing method.

EXAMPLE 1

*Cryptosporidium* and *Giardia*

*Cryptosporidium parvum* oocysts were purified from pooled faeces of naturally infected neonatal calves in Sydney. Faecal samples were centrifuged (2000 g, 10 min) and resuspended in water twice and then resuspended in 5 volumes of 1% (w/w) $NaHCO_3$. Fatty substances were then extracted twice with 1 volume of ether, followed by centrifugation (2000 g for 10 min). Pellets were resuspended in water and filtered through a layer of pre-wetted non-adsorbent cotton wool. The eluate was overlaid onto 10 volumes of 55% (w/v) sucrose solution and centrifuged (2000 g for 20 min). Oocysts were collected from the sucrose interface and the sucrose flotation step repeated until no visible contaminating material could be detected. Purified oocysts were surface sterilised with ice cold 70% (v/v) ethanol for 30 min, washed once in phosphate buffered saline (150 m mol $l^{-1}$ NaCl, 15 m mol $l^{-1}$ $KH_2PO_4$, 20 m mol $l^{-1}$ $Na_2HPO_4$, 27 m mol $l^{-1}$KCl, pH 7.4) (PBS), and diluted in PBS to a concentration of approximately $1\times10^7$ oocysts $ml^{-1}$ and stored at 4° C.

*Giardia lamblia* cysts were purchased from Waterborne Inc (New Orleans, USA).

Inactivation of *Cryptosporidium* and *Giardia* Stock

Suspensions of cysts and oocysts were diluted separately in 0.1M phosphate buffered saline solution to a concentration of approximately $2\times10^5$ organisms per ml (as determine by flow cytometric enumeration). Aliquots (2 mLs) of each suspension were placed in separate 12×75 Falcon tubes. The tubes were capped and then exposed to =>200,000 rads of gamma radiation to ensure inactivation of the microorganisms. Tubes were labeled as inactivated stock and stored at 4° C. (+/−4° C.) until used.

Instrumentation

A Becton Dickinson FACSCalibur flow cytometer was used for analysis and: cell sorting. An apparatus designed specifically for collecting microorganisms sorted by a Becton Dickinson FACSCalibur flow cytometer was attached to the, flow cytometer prior to starting the instrument.

The apparatus consists of a FRAC100 fraction collector (Pharmacia Ltd), silicon tubing of approximately 25 cm in length, a modified Macintosh computer mouse and electrical cables.

Each time the fraction collector positions a new tube in the collection area an electronic pulse is sent to an output socket on the back of the collector. This electric pulse was used to signal the flow cytometer to begin cell sorting.

Normally the flow cytometer is triggered into sorting the specified number of microorganisms, by moving the mouse icon over the "acquire" function button in the cytometer control software and then pressing the mouse button. In the modified mouse circuit, the mouse button switch was bypassed, and replaced with an opto-coupler. The transistor side of the opto-coupler performs the switching when the signal (5 volt logic) from the fraction collector arrives at the input. A 9 volt battery was used to maintain the voltage across the transistor side of the opto-coupler at a level just below the switching voltage. A diode was inserted between the battery and the transistor to decrease the voltage applied to the transistor from the 9 volt battery. The modified mouse was connected to the cytometer by inserting the mouse lead into the normal mouse port. An electrical lead was connected between the signal output socket on the fraction collector and the input of the modified mouse circuit.

To attach the apparatus to the fluidics system of the, cytometer the following sequence was carried out:
1) The cytometer hood was opened
2) The flow-cell optical shield was removed
3) The pre-existing sort-tube was removed
4) The dispensing apparatus was attached to the base of the cytometer
5) The dispensing apparatus sort-tube was attached to the cytometer sort-head
6) The flow-cell optical shield was replaced.

To initialize the carousel the following sequence was carried out:
1) The carousel power supply was turned on.
2) A value of 0.10 was entered as the fraction size.
3) The carousel was filled with 6 ml plastic test tubes.
4) The dispenser arm is positioned over the first test tube.

To configure the cytometer the following sequence was performed:
1) The cytometer was started as per users manual (Becton Dickinson, San Jose, USA).
2) The SHEATH tank is filled with Isoton (Coulter Pty Ltd, Brookvale) and then degassed by placing in a bell jar and applying a vacuum to the bell jar for 30 minutes.
3) The sheath tank is connected to the cytometer and the cytometer is put through two PRIME cycles.
4) A dot-plot of PSC versus SSC was displayed.
5) A logarithmic amplifier was selected for all detectors.

Dispensing *Cryptosporidium*
1) A sample of the inactivated *Cryptosporidium* stock was loaded and run on the low flow rate setting.
2) The voltages to the FSC and SSC detectors were adjusted until the population of oocysts appeared in the centre of the dot-plot.
3) The threshold rate was adjusted until the threshold level was slightly below the oocyst population.
4) A circular region (R1) was drawn around the population of oocysts.
5) The cytometer was set to sort 100 particles that appear in region R1 in SINGLE CELL mode.
6) The cursor on the, computer screen was positioned on the AQUIRE button.
7) RUN was pressed on the fraction collector.

Once sorting into all 96 tubes was complete the sample of inactivated *Cryptosporidium* stock was removed from the cytometer and the cytometer was cleaned by running a sample of 10% sodium hypochlorite for 5 minutes.

Dispensing Giardia

1) A sample of the inactivated Giardia stock was loaded and run on the low flow rate setting.
2) The threshold rate was adjusted until the threshold level was slightly below the cyst population.
3) Region (R1) was positioned over the population of oocysts.
4) The cytometer was set to sort 100 particles that appear in region R1 in SINGLE CELL mode.
5) The cursor on the computer screen was positioned on the AQUIRE button.
6) The fraction collector dispenser arm was positioned over the first test tube.
7) RUN was pressed on the fraction collector.

Once sorting into all 96 tubes was complete the tubes were capped, placed in racks at 4° C. and gamma irradiated within 8 hours.

Sterilisation of Tubes

The test tubes containing the sorted *Cryptosporidium* oocysts and Giardia cysts were exposed to=>200,000 rads of gamma radiation and then stored at 4° C.

Quality Control

Five percent of the test tubes produced (evenly spaced throughout the production run) were analysed to ensure that the correct number of *Giardia* and *Cryptosporidium* are in each tube.

Fluoroscein isothiocyanate (FITC) labeled *Cryptosporidium*-specific and *Giardia*-specific monoclonal antibodies were filtered (0.22 μm) and then 100 μl added to each test tube. After incubation at room temperature for 15 minutes samples were analysed using flow cytometry and the number of cysts and oocysts within each tube recorded.

The mean and standard deviation for the number of cysts and oocysts in the tubes tested was determined and recorded.

All test tubes that were produced were weighed and tubes were discarded that were 0.1 g greater or less than the median weight of all the tubes.

Using the Control Samples

The control samples of *Cryptosporidium* oocysts and *Giardia* cysts were used to perform quality control of an immunomagnetic separation procedure and a flow cytometry method used by a commercial laboratory for testing water samples for the presence of *Cryptosporidium* and *Giardia*.

Fifty test tubes of control samples were added to reagent grade water and analysed using the immunomagnetic separation procedure and the flow cytometry method. Results were expressed as percentage recovery using the following formula:

(number detected/mean of control material)×100

The average recovery of *Cryptosporidium* oocysts and *Giardia* cysts from the 50 reagent grade water samples analysed, were 82%±18 and 72%±16 respectively.

REFERENCES

Reynolds, D. T., Slade, R. B., Sykes, N. J., Jonas, A. and Fricker, C. R. 1999. Isolation of *Cryptosporidium* Oocysts from Water: How Can Precise Recovery Data be Generated? J. Appl. Microbiol. in press.

Shapiro, H. M., 1995. *A practical guide to flow cytometry*, third edition. A. R. Liss, New York.

Vesey, G., Hutton, P. E., Champion, A. C., Ashbolt, N. J., Williams, K. L., Warton, A, and Veal, D. A., 1994a. Application of flow cytometric methods for the routine detection of *Cryptosporidium* and *Giardia* in water. *Cytometry,* 16, 1–6.

Vesey, G.; Narai, J; Ashbolt, N., Williams, K. L. and Veal, D. A. 1994b. Detection of specific microorganisms in environmental samples using flow cytometry. In: *Methods in Cell Biology, Volume* 42—*Flow Cytometry Second Edition*. ed. Darzynkiewicz, Z., Robinson; J. P. and Crissman, H. A. pp. 489–522, Academic Press Inc., N.Y.

The invention claimed is:

1. A process for automated preparation of control samples containing a predetermined number of desired particles, comprising:
   providing a sample of particles;
   separating a predetermined number of desired particles from the sample by a particle separator;
   positioning by a collecting apparatus a receptacle or a surface capable of retaining particles to receive the predetermined number of desired particles; and
   dispensing the predetermined number of particles separated by the particle separator into the receptacle or onto the surface in accordance with a sorting instruction from the collecting apparatus;
   wherein the sorting instruction is sent from the collecting apparatus to the particle separator via a modified mouse circuit which activates software controlling the particle separator through an onscreen function button such that when a sorting instruction has been actuated the predetermined number of particles is delivered into the receptacle or onto the surface which is positioned for sufficient time to collect the particles by the collecting apparatus, following collection the collecting apparatus advances and positions a subsequent receptacle or surface for receipt of a subsequent particle, the collecting apparatus thereafter signaling the particle separator via the modified mouse to commence another sorting instruction.

2. The process according to claim 1 wherein the particles are selected from the group consisting of cells, bacteria, protozoa, yeast, fungi, spores, pollen, and viruses.

3. The process according to claim 2 wherein the cells are animal or plant cells.

4. The process according to claim 1 wherein the particle separator is an automated liquid separator selected from the group consisting of flow cytometer, coulter particle separating apparatus, and optical particle separator.

5. The process according to claim 4 wherein the particle separator is a flow cytometer.

6. The process according to claim 1 wherein the collecting apparatus is a fraction collector.

7. The process according to claim 1 wherein the particle separator and the collecting apparatus communicate electronically such that movement of the receptacle or surface into a position to receive the dispensed separated particles sends a sorting instruction in the form of an electric signal from the collecting apparatus to the particle separator via the modified mouse circuit.

8. A process according to claim 1 wherein the sorted particles forming the control sample are irradiated by gamma radiation or UV radiation.

9. A process for automated preparation of control samples containing a predetermined number of desired microorganisms or cells, comprising:
   providing a sample of microorganisms or cells;
   separating a predetermined number of desired microorganisms or cells from the sample by a cell separator;
   positioning by a collecting apparatus a receptacle or a surface capable of retaining microorganisms or cells to receive the predetermined number of desired microorganisms or cells; and
   dispensing the predetermined number of microorganisms or cells separated by the cell separator into the receptacle or onto the surface in accordance with a sorting instruction from the collecting apparatus;
   wherein the sorting instruction is sent from the collecting apparatus to the particle separator via a modified mouse circuit which activates software controlling the cell separator through an onscreen function button such that when a sorting instruction has been actuated the predetermined number of microorganisms or cells is delivered into the receptacle or onto the surface which is positioned for sufficient time to collect the microorganisms or cells by the collecting apparatus, following collection the collecting apparatus advances and positions a subsequent receptacle or surface for receipt of subsequent microorganisms or cells, the collecting apparatus thereafter signaling the cell separator via the modified mouse to commence another sorting instruction.

10. The process according to claim 9, further comprising irradiating the control samples with gamma or UV radiation.

11. The process according to claim 9, further comprising analysing a percentage of the control samples to confirm the number of microorganisms or cells.

12. The process according to claim 9, further comprising weighing the control samples as an additional quality control procedure.

13. The process according to claim 9, further comprising using the control samples to determine the efficiency of a testing method.

14. The process according to claim 9, further comprising staining the control samples with a marker to differentiate target microorganisms or cells from contaminating particles contained in the sample.

15. The process according to claim 14 wherein the staining is accomplished with a fluorescent marker.

16. A process according to claim 9 wherein the sorted microorganisms or cells forming the control sample are irradiated by gamma irradiation or UV irradiation.

* * * * *